(12) United States Patent
Lan et al.

(10) Patent No.: US 8,202,553 B2
(45) Date of Patent: Jun. 19, 2012

(54) METHODS AND COMPOSITIONS FOR TREATING BLOOD CIRCULATION DISORDERS

(76) Inventors: Guihua Lan, Yunnan Province (CN); Peng Chen, Yunnan Province (CN); Feng Lan, Yunnan Province (CN); Song Fang, Yunnan Province (CN)

( * ) Notice: Subject to any disclaimer, the term of this patent is extended or adjusted under 35 U.S.C. 154(b) by 267 days.

(21) Appl. No.: 12/651,251

(22) Filed: Dec. 31, 2009

(65) Prior Publication Data

US 2011/0160153 A1    Jun. 30, 2011

(51) Int. Cl.
*A01N 65/00* (2009.01)

(52) U.S. Cl. ............................................ 424/725
(58) Field of Classification Search .................. None
See application file for complete search history.

(56) References Cited

FOREIGN PATENT DOCUMENTS

CN        1954828    *   5/2007

* cited by examiner

*Primary Examiner* — Michael Meller
(74) *Attorney, Agent, or Firm* — Daniel W. Celander; Celander Law Firm Ltd.

(57) ABSTRACT

Methods for preparing improved *Panax Notoginseng* saponin fraction from a Sanchi extract and its use in pharmaceutical compositions for treating or preventing a blood circulation disorder.

6 Claims, No Drawings

METHODS AND COMPOSITIONS FOR TREATING BLOOD CIRCULATION DISORDERS

BACKGROUND

The Chinese herb, *Panax Notoginseng* (Burk.) F. H. Chen, is known for its beneficial pharmacological actions on the cardiovascular system. *Panax Notoginseng*, which is also known as Sanchi or Tienchi, grows in Yunnan and Guangxi Provinces of China. The active ingredients of the Sanchi plant are the *Panax Notoginseng* saponins (PNS). Thus far, researchers have identified and characterized twenty different dammarane-type saponins extracted from the Sanchi plant, many of which are pharmacologically active substances. For example, two major pharmacologically active saponins, panoxadiol and panoxatriol, are generated following hydrolysis of the ginsenoside monomer present in PNS.

The cardiovascular pharmacology of PNS preparations has been well studied. PNS preparations protect cardiac muscle and vascular endothelium by reducing the surface activity of blood platelets, by enhancing resistance to oxidative damage, and by removing free radical oxygen species. These effects of PNS preparations are thought to improve heart function and blood circulation and to promote greater tolerance to hypoxia conditions. Consequently, PNS preparations are useful for treating or preventing high blood pressure, hyperlipemia disease, and ischemic heart disease.

Though crude Sanchi extracts offer these health benefits, PNS preparations produced from Sanchi extracts offer several advantages over crude Sanchi extracts, including greater stability, higher bioavailability, lower toxicity, and improved safety. However, PNS preparations are available today that have reduced potency and inferior quality when used in the clinical setting.

The common drawbacks to presently available PNS preparations concern their low purity and the presence of contaminants. Furthermore, currently available PNS preparations are contaminated with unacceptable amounts of toxic metals, such as lead, arsenic, and mercury and can't wipe them off.

Some of these drawbacks are attributed to the relatively complex production processes for PNS preparations. Moreover, these production processes are used to generate PNS preparations for injection that are of dubious quality due to the presence of the aforementioned toxic substances. Thus, concerns exist about the safe administration of these compositions to patients.

Thus, there is a long-felt need for improved purification methods that yield highly purified PNS preparations suitable for administration to patients for treating or preventing blood circulation disorders, including cardiovascular disease.

SUMMARY

In a first aspect, the invention is a method of treating or preventing a blood circulation disorder in a mammal, comprising administering to said mammal a pharmaceutical composition comprising or formulated using a therapeutically effective amount of a Sanchi extract comprising greater than 60% (wt/wt) *Panax Notoginseng* saponin fraction.

In a second aspect, the invention is a pharmaceutical composition for treating or preventing a blood circulation disorder, wherein the pharmaceutical composition comprises a Sanchi extract comprising greater than 60% (wt/wt) *Panax Notoginseng* saponin fraction, an excipient, and a pharmaceutically acceptable carrier.

In a third aspect, the invention is a method for preparing a *Panax Notoginseng* saponin fraction, comprising extracting a crushed preparation of Sanchi with ethanol to obtain a first extract; processing the first extract on a first chromatographic resin to obtain a second extract; and decolorizing the second extract on a second chromatographic resin to obtain a third extract, wherein the third extract is the *Panax Notoginseng* saponin fraction.

DETAILED DESCRIPTION

The goal of this invention is to provide improved methods for purifying *Panax Notoginseng* saponins ("PNS preparations") from the Sanchi herb that would be suitable for use in pharmaceutical compositions for treating or preventing blood circulation disorders. The disclosed purification methods are simple and robust, offering improvements in both yield and quality of the PNS preparations than have been obtained previously from crude Sanchi extracts. The methods and compositions of the present invention satisfy an un-met, long-felt need regarding high quality PNS preparations and their use for treating or preventing blood circulation disorders, including cardiovascular disease.

The Sanchi extract is prepared by the following procedure. The Sanchi is initially crushed by conventional mechanical means (for example, mortar and pestle, blender, roller press, ball bearing, milling, muller, grinding mill, hammer mill, or the like). Preferably, the crushed Sanchi material is a fine powder-like material. This Sanchi extract material is prepared using a muller.

The resultant Sanchi material is extracted with 50% (vol/vol) to 90% (vol/vol) aqueous ethanol. The preferred alcohol extraction method employs 70% (vol/vol) aqueous ethanol. The Sanchi powder is subjected to three rounds of extraction with aqueous ethanol, wherein each round of extraction uses an amount of ethanol (by volume) that is six-fold the amount of Sanchi powder (by weight). Preferably, each round of extraction of the Sanchi powder is done under ethanol-reflux conditions at 80° C. for two hours.

A round of extraction of the Sanchi powder typically comprises contacting the Sanchi powder with an extraction fluid for a designated period of time. Contacting preferably includes exposing the Sanchi powder to the extraction fluid and includes subjecting the Sanchi powder/fluid mixture to mechanical agitation, such as mixing, rolling, vortexing, blending, slurrying, refluxing and the like. Preferably, contacting is exposing the Sanchi powder to the extraction fluid by refluxing at elevated temperature, such as 70° C. to 85° C. Even more preferably, contacting is exposing the Sanchi powder to the extraction fluid by refluxing at 80° C. Mechanical agitation by refluxing enables maximum extraction of the PNS from the Sanchi powder, thereby producing an extraction liquid containing PNS.

Following each round of extraction, the Sanchi powder is recovered from the extraction fluid by performing a separation step, such as centrifugation, filtration, or an equivalent process. The Sanchi powder is preferably filtered following each round of extraction. The extraction fluid containing the PNS is filtered through any suitable means (for example, paper filter, sieve, fine mesh screen, or the like).

The recovered Sanchi powder is subjected to additional rounds of extraction until three rounds of extraction are completed. The three filtrates are then combined and concentrated to achieve a relative density of 1.15 to 1.2.

The resultant concentrate is diluted by adding three volumes of water to provide an aqueous-ethanol mixture. This mixture is filtered thereafter to remove any precipitates that may be present to obtain a first extract.

The resultant first extract is then applied to a macroporous adsorption resin equilibrated with a suitable chromatography medium (for example, pure water). Preferably, the macroporous adsorption resin is functionalized with a weakly polar styrene divinylbenzene skeleton. Most preferably, the macroporous adsorption resin is D101-1. Following loading of the entire first extract onto the macroporous adsorption resin, the resin is washed initially with water and washed subsequently with two volumes of 20% (vol/vol) aqueous ethanol per volume of resin to further remove contaminants. The PNS material is eluted from the resin using 50% (vol/vol) to 80% (vol/vol) aqueous ethanol to provide a second extract.

The second extract containing the PNS is then applied to a decolorizing resin to remove impurities that may bind to the resin. The decolorized PNS preparation obtained in the flow-thru from the decolorizing resin provides a third extract.

Preferably, the decolorizing resin is an anion exchange resin. Most preferably, the decolorizing resin is a D900 anion exchange resin.

A dried form of the PNS preparation is obtained following removal of the residual solvent present in the third extract. The residual solvent is removed preferably by initially concentrating the third extract to obtain a reduced-volume concentrate and spray drying the resultant concentrate to dryness.

It is desirable to reduce the contents of some poisonous substances, such as the toxic metals like lead, arsenic, and mercury, which may be present in crude Sanchi extracts for large-scale purification of the PNS preparations. These metals are preferably removed from the PNS preparation after the third extract is obtained from the ion exchange decolorizing resin chromatography procedure. Such metals are preferably removed by applying the third extract to a chelate resin to permit removal of these metals. The resultant flow-through fraction from the chelate resin chromatography represents a fourth extract that includes the PNS preparation substantially free of toxic metal substances. The PNS preparation of the fourth fraction is typically concentrated and dried as described previously for the third extract.

The present invention contemplates pharmaceutical or nutraceutical compositions of PNS preparations for administration to mammals to treat blood circulation disorders, cardiovascular diseases, and related conditions. In a preferred embodiment, a composition for administration is a pharmaceutical or nutraceutical composition, preferably in a single unit dosage form. Pharmaceutical or nutraceutical compositions and single unit dosage forms can comprise a prophylacticly or therapeutically effective amount of one or more prophylactic or therapeutic agents, and a typically one or more pharmaceutically acceptable carriers or excipients or diluents.

The term "pharmaceutically acceptable" means approved by a regulatory agency of the Federal or a state government (for example, the U.S. Food and Drug Administration) or listed in the U.S. Pharmacopeia or other generally recognized pharmacopeia for use in animals, and more particularly in humans.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Examples of suitable pharmaceutical carriers are described in "Remington's Pharmaceutical Sciences" by E. W. Martin. Nutraceutical compositions can, but need not, comprise one or more active or inactive ingredients that are not necessarily considered pharmaceutically acceptable to current practitioners in the art.

A pharmaceutical or nutraceutical composition of the invention can be administered by any route according to the judgment of those of skill in the art, including but not limited to orally, intravenously, intragastrically, intraduodenally, intraperitoneally or intracerebroventricularly.

Typical pharmaceutical or nutraceutical compositions and dosage forms comprise one or more excipients. Suitable excipients are well-known to those skilled in the art of pharmacy, and non-limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical or nutraceutical composition or dosage form depends on a variety of factors well known in the art including, but not limited to, the way in which the dosage form will be administered to a patient and the specific active ingredients in the dosage form. The composition or single unit dosage form, if desired, can also contain minor amounts of wetting or emulsifying agents, or pH buffering agents.

The invention further encompasses administration of pharmaceutical or nutraceutical compositions and single unit dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

The pharmaceutical or nutraceutical compositions and single unit dosage forms can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Such compositions and dosage forms will contain a prophylactically or therapeutically effective amount of a PNS preparation, together with a suitable amount of carrier so as to provide the form for proper administration to the patient.

The formulation should suit the mode of administration. In a preferred embodiment, the pharmaceutical or nutraceutical compositions and single unit dosage forms are sterile and prepared in a form suitable for administration to a subject, preferably an animal subject, more preferably a mammalian subject, and most preferably a human subject. Besides humans, preferred animal subjects include horses, birds, cats, dogs, rats, hamsters, mice, guinea pigs, cows, and pigs.

A pharmaceutical or nutraceutical composition of the invention is formulated to be compatible with its intended route of administration. Examples of routes of administration include, but are not limited to, parenteral, e.g., intravenous, intradermal, subcutaneous, intramuscular, subcutaneous, oral, buccal, sublingual, inhalation, intranasal, transdermal, topical, transmucosal, intra-tumoral, intra-synovial and rectal administration. In a specific embodiment, the composition is formulated in accordance with routine procedures as a pharmaceutical or nutraceutical composition adapted for intravenous, subcutaneous, intramuscular, oral, intranasal or topical administration to human beings. In an embodiment, a pharmaceutical or nutraceutical composition is formulated in accordance with routine procedures for oral administration to human beings. Typically, compositions for oral administration are solid dosage forms or solutions in sterile isotonic aqueous buffer.

Examples of dosage forms include, but are not limited to: tablets; caplets; capsules, such as soft elastic gelatin capsules or hard capsules; dropping pills; cachets; troches; lozenges; dispersions; suppositories; ointments; cataplasms (poultices); pastes; powders; dressings; creams; plasters; solutions; patches; aerosols (for example, nasal sprays or inhalers); gels; liquid dosage forms suitable for oral or mucosal administration to a patient, including suspensions (for example, aqueous or non-aqueous liquid suspensions, oil-in-water emulsions, or a water-in-oil liquid emulsions), solutions, and elixirs; liquid dosage forms suitable for parenteral or intravenous administration to a patient; and sterile solids (for example, crystalline or amorphous solids or granular forms) that can be reconstituted to provide liquid dosage forms suitable for parenteral or intravenous administration to a patient.

The composition, shape, and type of dosage forms of a PNS preparation will typically vary depending on their use. For example, a dosage form used in the acute treatment of a blood disorder may contain larger amounts of one or more of a PNS preparation than a dosage form used in the chronic treatment of the same disease. Also, the therapeutically effective dosage form may vary among different types of diseases or disorders. Similarly, a parenteral dosage form may contain smaller amounts of one or more of the active than an oral dosage form used to treat the same disease or disorder. These and other ways in which specific dosage forms encompassed by this invention will vary from one another will be readily apparent to those skilled in the art. See, e.g., Remington's Pharmaceutical Sciences, 18th ed., Mack Publishing, Easton Pa. (1990).

Generally, the ingredients of compositions comprising a PNS preparation are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Pharmaceutical or nutraceutical compositions used in the methods of the invention that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington's Pharmaceutical Sciences, 18th ed., Mack Publishing, Easton Pa. (1990).

In certain embodiments, the oral dosage forms are solid and prepared under anhydrous conditions with anhydrous ingredients, as described in detail in the sections above. However, the scope of the invention extends beyond anhydrous, solid oral dosage forms. As such, further forms are described herein.

Typical oral dosage forms are prepared by combining the active ingredient(s) (that is, the PNS preparation) in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Examples of fillers suitable for use in the pharmaceutical or nutraceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. An specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrants that can be used in pharmaceutical or nutraceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, pre-gelatinized starch, other starches, clays, other algins, other celluloses, gums, and mixtures thereof.

Lubricants that can be used in pharmaceutical or nutraceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

The amount of the composition in the methods of the invention which will be effective in the prevention, treatment, management, or amelioration of a blood circulation disorder or one or more symptoms thereof will vary with the nature and severity of the disease or condition, and the route by which the active ingredient is administered. The frequency and dosage will also vary according to factors specific for each patient depending on the specific therapy (e.g., therapeutic or prophylactic agents) administered, the severity of the disorder, disease, or condition, the route of administration, as well as age, body, weight, response, and the past medical history of the patient. Effective doses may be extrapolated from dose-response curves derived from in vitro or animal model test systems.

Typical dosage forms for administration in methods of the invention comprise a composition of the invention in an amount within the range of from about 0.001 mg to about 500 mg of PNS per day, 0.10 mg to 300 mg PNS per day, or 1.0 mg to 200 mg of PNS per day given as a single once-a-day dose or as divided doses throughout the day. Particular dosage forms of the invention have incremental variations from about 0.001, 0.01, 0.1, 0.2, 0.25, 0.3, 0.5, 0.75, 1.0, 2.0, 2.5, 3.0, 5.0, 7.5, 10.0, 15.0, 20.0, 25.0, 40.0, 50.0, 60.0, 75.0, 100, 125, 150, 175, 200, 250, 300, 400, and 500 mg of PNS, as well as incremental dosage variations thereof.

Exemplary dosage forms of the invention having a liquid formulation include 1, 3, 5, 7.5, 10, 15, 20, 50, 75, and 100 ml of a liquid composition of PNS having a concentration ranging from about 0.01 μg/ml to about 500 mg/ml. The preferred concentrations of such PNS liquid compositions will depend upon the dissolution characteristics of the medium, which will determine the upper limit of pharmaceutically acceptable concentrations of PNS in such compositions. Consequently, alternative, pharmaceutically acceptable, concentrations of PNS liquid compositions that are lower, as well as higher, than that stated herein are also contemplated by the present invention.

In the case of liquid dosage forms, suitable concentrations of PNS are suspended or dissolved in pharmaceutically acceptable carrier media, such as water, saline, and the like. Furthermore, suitable concentrations of PNS are suspended or dissolved under physiologically and physiochemically appropriate conditions.

The term "PNS fraction" refers to a PNS preparation obtained from a Sanchi plant extract using the purification methods of the invention. The percentage PNS fraction, such as 65% PNS fraction, refers to the amount of PNS present in a PNS preparation obtained following purification and reflects percentage weight of a given PNS preparation that represents pure PNS. For examples, about 100 mg of a 65% PNS fraction would include about 65 mg of PNS, while about 100 mg of a 95% PNS fraction would include about 95 mg of PNS.

The aforementioned amounts and concentrations of PNS preparations refer to a Sanchi extract comprising greater than 60% (wt/wt) PNS fraction, as purified according to the methods of the invention. More preferably, PNS preparations suitable for use in compositions of the present invention refer to a Sanchi extract comprising by weight (wt/wt) from about 65% to about 99% PNS fraction, including 70%, 75%, 80%, 85%, 90%, and 95% PNS fraction, as well as incremental fractions thereof.

Dosage regimens are adjusted predictably and routinely to compensate for PNS preparations having differing extents of potency based upon the purity of PNS preparation used, which is well within the purview and understanding of the skilled artesian. For example, a dose containing about 100 mg of a 65% PNS fraction would be expected to have the same potency as a dose containing about 68.4 mg of a 95% PNS fraction, because about 65 mg of PNS would be present in each dose.

Exemplary doses of a composition of the invention include microgram or milligram amounts of PNS per kilogram of subject or sample weight. For a composition used in the invention, the dosage administered to a patient can be administered from about 0.001 mg/kg to about 10 mg/kg. In certain embodiments, the dosage is from about 0.02 mg/kg to about 4.0 mg/kg of the patient's body weight, based on weight and purity of the PNS preparation in the composition.

The composition can be administered as a single once-a-day dose or as divided doses throughout a day. In some embodiments, the daily dose is administered twice daily in equally divided doses. In other embodiments, the daily dose is administered three times per day. In particular embodiments, the daily dose is administered three times per day in equally divided doses. In particular embodiments, the daily dose is administered four times per day in equally divided doses. The actual dosage can be determined by a practitioner of skill in the art according to, for example, the subjects age, body weight, body mass index, or other factors.

In certain embodiments, administration of a composition in the invention may be repeated daily. In certain embodiments and the administrations may be separated by at least 1 day, 2 days or 3 days.

An effective amount of a composition described herein will provide therapeutic benefit without causing substantial toxicity. Toxicity of a composition can be determined by standard pharmaceutical procedures in cell cultures or experimental animals, for example, by determining the $LD_{50}$ (that is, the dose lethal to 50% of the population) or the $LD_{100}$ (that is, the dose lethal to 100% of the population).

The therapeutic index is the dose ratio between therapeutic effect and toxicity effect. Compounds which exhibit high therapeutic indices are preferred. The data obtained from these cell culture assays and animal studies can be used in formulating a dosage range that is not toxic for use in humans. The dosage of the compounds described herein lies preferably within a range of circulating concentrations that include the effective dose with little or no toxicity. The dosage may vary within this range depending upon the dosage form employed and the route of administration utilized. The exact formulation, route of administration and dosage can be chosen by the individual physician in view of the patient's condition and the indication to be treated. (See, e.g., Fingl et al., 1996, In: The Pharmacological Basis of Therapeutics, 9.sup.th ed., Chapter 2, p. 29, Elliot M. Ross).

The descriptions of exemplary doses are merely alternative descriptions that may be used optionally at the discretion of the physician and are not intended to conflict or supercede other descriptions of doses disclosed herein. The pharmacological action of PNS preparations of the invention is demonstrated by the following examples for preventing or treating blood circulation disorders.

Example 1

The Effect on Cerebral Vascular Resistance of Cat

Cats weighing 2.9-3.1 kg were anaesthetized. One of the common carotid arteries in each animal were separated and the branches were linked to the input end of constant flow pump, while the end of the common carotid artery nearer the heart was linked to the output end of constant flow pump so that continuous blood flow into brain was regulated by the constant flow pump. Quicksilver manometers were placed at both the input end and output end to record blood pressure and cerebral vascular resistance. The constant flow pump was adjusted under constant temperature to ensure that the blood pressure maintained the cerebral vascular resistance. The animals were administered intravenously with 50 mg/kg or 100 mg/kg of a PNS preparation purified from a Sanchi extract (for example, a 65% PNS fraction) after the blood pressure and cerebral vascular resistance was stable. The change in cerebral vascular resistance and blood pressure were recorded before and after the PNS preparation was administered to the animals. The results are presented in Table 1.

TABLE 1

Effect of PNS preparation on cerebral vascular resistance

| Treatment Group[a] | Dosage (mg/kg) | Initial CVR[b] (KPa) | % Decline CVR[d] |
|---|---|---|---|
| Control[c] | — | 11.64 ± 0.21 | 2.34 ± 0.29 |
| Sanchi extract[e] | 50 | 11.35 ± 0.13 | 9.00 ± 0.51* |
| Sanchi extract[e] | 100 | 11.30 ± 0.10 | 13.90 ± 0.79** |

[a]Each group consists of 28 cats.
[b]CVR, Cerebral Vascular Resistance,
[c]Control group received only physiological saline solution.
[d]Statistical significance, compared to control group,
*$P < 0.05$,
**$P < 0.01$.
[e]65% PNS fraction.

These results indicate that the PNS preparations of the present invention significantly reduce cerebral vascular resistance in the cat.

Example 2

The Effect on Cerebral Thrombosis of Rat

Large rats develop cerebral thrombosis with feeding. In this example, large rats were feed continuously with feed that contained either a PNS preparation made according to the present invention or a sham supplement.

Large rats of both genders weighing about 200 g were divided randomly into three groups. Each group was fed twice daily for fourteen days with feed that included a dose of PNS preparation (for example, 65% PNS fraction) or a sham supplement. The rats were sacrificed within one hour of the last feeding, and the wet weight of the thrombus was measured. The effect of the PNS on thrombus weight was determined by calculating the extent to which rats receiving PNS displayed lower thrombus weights relative to rats receiving sham supplement in their feed. The results are presented in Table 2.

TABLE 2

The effect on cerebral thrombosis of big rat

| Treatment Group[a] | Dosage (mg/kg) | Thrombus Wt. (mg) | % Suppression |
|---|---|---|---|
| Control[b] | — | 51.24 ± 5.69 | — |
| Sanchi extract[c] | 10 | 45.26 ± 7.20 | 11.67 |
| Sanchi extract[c] | 20 | 43.49 ± 9.52 | 15.12 |

[a]Each group included 28 rats.
[b]Control group received only physiological saline solution.
[c]65% PNS fraction.

These results indicate that the PNS preparation of the present invention reduce thrombosis in the rat and displays a dose-dependent reduction in this regard.

Example 3

The Effect of PNS Preparations for Treating Coronary Heart Disease and Angina Pectoris in Humans Two hundred thirty patients were divided randomly into two groups. The group to receive the PNS preparation ("treatment group") included 130 patients. This group is composed of 88 males and 42 females having an average age of 62±9 years old. The patients of this group had some form of cardiovascular disease for 2-10 years and included 102 cases of exertional angina pectoris, 22 cases of spontaneous angina pectoris, 6 cases of variant angina pectoris, 31 cases of high blood pressure and 42 case of hyperlipemia, and 61 cases in which ischemic electrocardiogram changes were evident.

The other group of patients received the compound salvia miltiorrhiza ("comparator group") and included 100 patients. This group is composed of 68 males and 32 females having an average age of 60±7 years old. The patients of this group had some form of cardiovascular disease for 2-10 years and included 82 cases of exertional angina pectoris, 16 cases of spontaneous angina pectoris, 2 cases of variant angina pectoris, 24 cases of high blood pressure, 34 cases of hyperlipemia, and 47 cases in which ischemic electrocardiogram changes were evident.

The treatment group received daily intravenous injections of the PNS preparation (200 mg of a 65% PNS fraction in 4 mL saline mixed together with 500 ml of 10% (wt/vol) glucose) for a period of 20 days. The comparator group received daily intravenous injections of salvia miltiorrhiza (20 g/ml of salvia miltorrhiza diluted into 500 ml of 10% (wt/vol) glucose) for a period of 20 days. The relevant clinical parameters associated with cardiovascular liver and renal functions and any evidence of adverse symptoms (electrocardiology measurements, hemorheology, blood-fat, blut-routine-untersuching, urine routine, heart rate, blood pressure, liver function, and renal function) were evaluated for each patient before the medications were administered and again after the 20-day administration period concluded.

The results obtained with the treatment and comparator groups were analyzed from the standpoints of their clinical benefit for improving cardiovascular conditions. Among the treatment group participants, 62 patients had a marked improvement on cardiovascular health while 46 patients displayed a significant improvement in cardiovascular health. By contrast, 16 patients experienced no improvement in cardiovascular health and six patients suffered worsened cardiovascular health. Thus, the total effective rate of improved cardiovascular health for the treatment group was 83%. By way of comparison to the corresponding results obtained for the comparator group participant, the total effective rate of improved cardiovascular health for the comparator group was 68%. The difference between the treatment group and the comparator group was statistically significant (P<0.05).

The electrocardiogram results obtained with the treatment and comparator groups were also analyzed. Among the sixty-one patients of the treatment group who experienced changes in their ischemic electrocardiograms, 29 patients displayed marked improvement, 21 patients displayed some improvement, 9 patients displayed no improvement, and 2 patients displayed worsened changes in their ischemic electrocardiograms. The total effective rate of improved changes in ischemic electrocardiogram profiles for the treatment group participants was 82%.

Among the 47 patients of the comparator group who experienced changes in their ischemic electrocardiogram profiles, 15 patients displayed a marked improvement, 14 patients displayed a significant improvement, 15 patients experience no improvement, while three patients experienced worsened changes in their ischemic electrocardiogram profiles. Thus, the total effective rate for improved changes in ischemic electrocardiogram profiles for the comparator group was 62%. These results indicate that the difference observed in the ischemic electrocardiogram profiles for the treatment group and the comparator group is significant (P<0.05).

The hemorheology profile is one of the important factors that affect the blood supply to the coronary artery. If the blood viscosity is too high, it can easily cause myocardial ischemia. Decreases in blood viscosity, total cholesterol (TC) level, and triglyceride (TG) level reduce the occurrence of coronary heart disease and improve the ischemic electrocardiogram profile.

Every index of hemorheology that was measured for the treatment group displayed significant decreases following treatment (P<0.01). The PNS treatment had no significant effect on blood corpuscle specific volume, plasma thromboplastin component, or blood platelet packing fraction. The hemorheology results indicate that the PNS preparation of the present invention significantly reduced TC levels and TG levels (P<0.01).

While the TC level, the whole blood specific viscosity, and the blood plasma specific viscosity of the comparator group declined significantly after administration (P<0.01), this group did not display comparably significant reductions in the TG level (P>0.01).

Example 4

The Effect of PNS Preparations on Diabetic Retinopathy of Optic Nerve Retina

Fifty-eight patients were selected for study, which included 36 males and 22 females having an age in the range of 8-88 years old. Among this group, 39 patients experienced optic nerve atrophy in one or both eyes, 14 patients experienced retinitis pigmentosa in both eyes, and 5 patients experienced macular degeneration in both eyes.

The course of the treatment was to inject 250 mg of PNS preparation (65% PNS fraction) behind the eye(s) having a pathological condition of the patient every other day for a total of 22 injections. All the patients experienced at least one eye having a pathological condition and received at least one course of treatment. Many patients, however, experienced a pathological condition in both eyes, which required two courses of treatment (that is, one for each eye).

All patients were examined for their cardiovascular function (electrocardiogram profile and blood pressure), liver function, and kidney function before they began treatment, and these clinical parameters were monitored for each patient during treatment. Patients received treatment only if they had no other contraindications.

The effect of the treatment was evaluated using the international eye examination test chart for each patient before the treatment course began and after the treatment course concluded. If the patient was able to read greater than three additional lines after treatment than possible before treatment, then the treatment was adjudged to have a marked effect on eye function. If the patient was able to read one to three additional lines after treatment than possible before treatment, then the treatment was adjudged to have a significant effect on eye function. If the patient was able to read less than one additional line after treatment than possible before treatment, then the treatment was adjudged to have marginal improvement on eye function. If the patient was unable to read any additional lines after treatment than possible before treatment or lost the ability to retain vision at previously established levels, then the treatment was adjudged to have no effect. The effects of PNS preparations on different eye pathologies are summarized in Table 3.

TABLE 3

The effect of PNS on different eye diseases.

| Pathology | Eye # | Eye Condition following treatment | | | | Effective Rate (%) |
|---|---|---|---|---|---|---|
| | | Marked | Significant | Marginal | None | |
| Macular degeneration | 10 | 1 | 6 | 1 | 2 | 80 |
| Retinitis pigmentosa | 28 | 2 | 15 | 5 | 6 | 79 |
| Optic Nerve Atrophy | 73 | 5 | 11 | 14 | 43 | 41 |
| Total | 111 | 8 | 32 | 20 | 51 | 54 |

The measured cardiovascular parameters (for example, blood pressure and electrocardiogram profile), liver function, and kidney function fell within normal ranges for the patients in the treatment group. Common side effects that some patients experienced included only slight disconformities of eyelid edema and bulbar conjunctival congestion. This demonstrates that the ocular administration route of the PNS was safe and effective.

While various embodiments of the invention have been described, it will be apparent to those of ordinary skill in the art that other embodiments and implementations are possible within the scope of the invention. Accordingly, the invention is not to be restricted except in light of the attached claims and their equivalents.

What is claimed is:

1. A method of treating optic nerve atrophy, macular degeneration or retinitis pigmentosa in a mammal in need thereof consisting essentially of administering to said mammal a therapeutically effective amount of an extract of Panax Notoginseng containing greater than 60% (wt/vol) of saponins.

2. The method of claim 1, wherein the mammal comprises at least one member selected from the group consisting of human, horse, bird, cat, dog, rat, hamster, mouse, guinea pig, cow, and pig.

3. The method of claim 1, wherein the therapeutically effective amount is formulated as a pharmaceutical composition comprising at least one member selected from the group consisting of a tablet, a capsule, a solution, a suspension, a dropping pill, an emulsion, a suppository, an enema, an injection formulation, and a dermal patch formulation.

4. The method of claim 1, wherein the extract of Panax Notoginseng contains greater than 80% (wt/vol) of saponins.

5. The method of claim 1, wherein the extract of Panax Notoginseng contains greater than 95% (wt/vol) of saponins.

6. The method of claim 1, wherein the therapeutically effective amount comprises 200 mg to 500 mg of an extract of Panax Notoginseng comprising 60% to 99% (wt/vol) of saponins.

* * * * *